(12) United States Patent
Le Neel et al.

(10) Patent No.: US 10,254,261 B2
(45) Date of Patent: Apr. 9, 2019

(54) INTEGRATED AIR QUALITY SENSOR THAT DETECTS MULTIPLE GAS SPECIES

(71) Applicant: STMicroelectronics Pte Ltd, Singapore (SG)

(72) Inventors: Olivier Le Neel, Singapore (SG); Tien Choy Loh, Singapore (SG); Shian Yeu Kam, Singapore (SG); Ravi Shankar, Singapore (SG)

(73) Assignee: STMicroelectronics PTE Ltd, Singapore (SG)

( * ) Notice: Subject to any disclaimer, the term of this patent is extended or adjusted under 35 U.S.C. 154(b) by 153 days.

(21) Appl. No.: 15/213,100

(22) Filed: Jul. 18, 2016

(65) Prior Publication Data

US 2018/0017536 A1    Jan. 18, 2018

(51) Int. Cl.
  *G01N 25/22* (2006.01)
  *G01N 33/00* (2006.01)

(52) U.S. Cl.
  CPC .......... *G01N 33/004* (2013.01); *G01N 25/22* (2013.01); *G01N 33/0047* (2013.01)

(58) Field of Classification Search
  CPC .................................................... G01N 33/004
  USPC ......................................................... 73/25.01
  See application file for complete search history.

(56) References Cited

U.S. PATENT DOCUMENTS

| | | | |
|---|---|---|---|
| 4,608,232 A | 8/1986 | Sunano et al. |
| 4,938,053 A | 7/1990 | Jepson et al. |
| 5,834,777 A | 11/1998 | Wong |
| 6,243,474 B1 | 6/2001 | Tai et al. |

(Continued)

FOREIGN PATENT DOCUMENTS

| CN | 201307027 Y | 9/2009 |
|---|---|---|
| CN | 102680016 A | 9/2012 |

(Continued)

OTHER PUBLICATIONS

Allen et al., "Associations of Cognitive Function Scores with Carbon Dioxide, Ventilation, and Volatile Organic Compound Exposures in Office Workers: A Controlled Exposure Study of Green and Conventional Office Environments," *Environmental Health Perspective (Online)* 124(6):805, Jun. 2016. (33 pages).

(Continued)

*Primary Examiner* — Walter L Lindsay, Jr.
*Assistant Examiner* — Philipmarcus T Fadul
(74) *Attorney, Agent, or Firm* — Seed IP Law Group LLP

(57) ABSTRACT

A microelectronic device capable of detecting multiple gas constituents in ambient air can be used to monitor air quality. The microelectronic air quality monitor includes a plurality of temperature-sensitive gas sensors tuned to detect different gas species. Each gas sensor is tuned by programming an adjacent heater. An insulating air pocket formed below the sensor helps to maintain the sensor at a desired temperature. A temperature sensor may also be integrated with each gas sensor to provide additional feedback control. The heater, temperature sensor, and gas sensors are in the form of patternable thin films integrated on a single microchip. The device can be incorporated into computer workstations, smart phones, clothing, or other wearable accessories to function as a personal air quality monitor that is smaller, more accurate, and less expensive than existing air quality sensors.

19 Claims, 13 Drawing Sheets

(56) References Cited

U.S. PATENT DOCUMENTS

| | | |
|---|---|---|
| 6,322,247 B1 | 11/2001 | Bonne et al. |
| 6,352,874 B1 | 3/2002 | McNeil et al. |
| 6,361,206 B1 | 3/2002 | Bonne |
| 6,383,832 B1 | 5/2002 | Nakabayashi |
| 6,478,974 B1 | 11/2002 | Lebouitz et al. |
| 6,546,812 B2 | 4/2003 | Lewis |
| 6,592,823 B1 | 7/2003 | Odermatt et al. |
| 6,698,297 B2 | 3/2004 | Gysling |
| 6,879,089 B2 | 4/2005 | Wong et al. |
| 7,280,436 B2 | 10/2007 | Pedersen |
| 7,437,951 B2 | 10/2008 | McDonald et al. |
| 7,556,895 B2 | 7/2009 | Moriya et al. |
| 7,703,339 B2 | 4/2010 | Sulouff, Jr. et al. |
| 7,821,085 B2 | 10/2010 | Suzuki et al. |
| 7,946,505 B2 | 5/2011 | Lynam et al. |
| 8,062,497 B2 | 11/2011 | Witvrouw et al. |
| 8,304,850 B2 | 11/2012 | Lazarov et al. |
| 8,390,121 B2 | 3/2013 | Okumura et al. |
| 8,487,387 B2 | 7/2013 | Lin et al. |
| 8,696,989 B2 | 4/2014 | Esfandyarpour et al. |
| 8,715,514 B2 | 5/2014 | Lee et al. |
| 8,806,933 B2 | 8/2014 | Kohno et al. |
| 8,852,513 B1 | 10/2014 | Speer et al. |
| 9,105,479 B2 | 8/2015 | Besling et al. |
| 9,164,052 B1 | 10/2015 | Speer et al. |
| 2002/0160611 A1 | 10/2002 | Horsley |
| 2002/0166376 A1 | 11/2002 | Kohmura et al. |
| 2003/0039299 A1 | 2/2003 | Horovitz et al. |
| 2003/0079542 A1 | 5/2003 | Bonne et al. |
| 2004/0008041 A1 | 1/2004 | Davis et al. |
| 2005/0109081 A1 | 5/2005 | Zribi et al. |
| 2005/0218465 A1 | 10/2005 | Cummins |
| 2006/0162466 A1 | 7/2006 | Wargo et al. |
| 2008/0163687 A1 | 7/2008 | Kranz et al. |
| 2008/0194053 A1 | 8/2008 | Huang |
| 2008/0308920 A1 | 12/2008 | Wan |
| 2008/0315332 A1 | 12/2008 | Kaelberer et al. |
| 2009/0218702 A1 | 9/2009 | Beyne et al. |
| 2009/0243003 A1* | 10/2009 | Renna ............... B81C 1/00158 257/414 |
| 2010/0173437 A1 | 7/2010 | Wygant et al. |
| 2010/0314740 A1 | 12/2010 | Choi et al. |
| 2011/0031565 A1 | 2/2011 | Marx et al. |
| 2011/0045639 A1 | 2/2011 | Masuko et al. |
| 2011/0108932 A1 | 5/2011 | Benzel et al. |
| 2011/0150261 A1 | 6/2011 | Ho et al. |
| 2011/0298134 A1 | 12/2011 | Williams et al. |
| 2012/0024054 A1 | 2/2012 | Huang et al. |
| 2012/0032283 A1 | 2/2012 | Frey et al. |
| 2012/0144921 A1 | 6/2012 | Bradley et al. |
| 2012/0167392 A1 | 7/2012 | Cherian et al. |
| 2012/0168882 A1 | 7/2012 | Cherian et al. |
| 2012/0171713 A1 | 7/2012 | Cherian et al. |
| 2012/0171774 A1 | 7/2012 | Cherian et al. |
| 2012/0299127 A1 | 11/2012 | Fujii et al. |
| 2012/0304742 A1 | 12/2012 | Cummins |
| 2013/0010826 A1 | 1/2013 | Le Neel et al. |
| 2013/0036806 A1 | 2/2013 | Kohno |
| 2013/0106813 A1 | 5/2013 | Hotelling et al. |
| 2013/0139587 A1 | 6/2013 | Le Neel et al. |
| 2013/0202489 A1 | 8/2013 | Ong et al. |
| 2013/0334620 A1 | 12/2013 | Chu et al. |
| 2014/0197500 A1 | 7/2014 | Guillemet et al. |
| 2014/0264655 A1 | 9/2014 | Williams et al. |
| 2014/0264744 A1 | 9/2014 | Chu et al. |
| 2014/0268523 A1 | 9/2014 | Gogoi |
| 2014/0291677 A1 | 10/2014 | Le Neel et al. |
| 2014/0291829 A1 | 10/2014 | Le Neel et al. |
| 2014/0292317 A1 | 10/2014 | Le Neel et al. |
| 2014/0294046 A1 | 10/2014 | Le Neel et al. |
| 2014/0311905 A1 | 10/2014 | Stetter et al. |
| 2014/0353773 A1 | 12/2014 | Loh et al. |
| 2015/0323510 A1* | 11/2015 | Huynh ............... H01L 23/3157 73/23.34 |
| 2016/0018356 A1 | 1/2016 | Shankar et al. |
| 2017/0016866 A1* | 1/2017 | Chey ................. G01N 33/0027 |
| 2017/0066646 A1* | 3/2017 | Cheng ................. G01L 9/0041 |
| 2017/0336343 A1 | 11/2017 | Bhat et al. |
| 2017/0370865 A1* | 12/2017 | Samarao ............. G01N 27/125 |
| 2018/0017513 A1 | 1/2018 | Le Neel et al. |

FOREIGN PATENT DOCUMENTS

| | | |
|---|---|---|
| CN | 102680018 A | 9/2012 |
| CN | 101788315 B | 11/2012 |
| CN | 202770456 U | 3/2013 |
| TW | 200531224 A | 9/2005 |
| WO | 2005/087471 A1 | 9/2005 |

OTHER PUBLICATIONS

World Health Organization, "7 million premature deaths annually linked to air pollution," News Release, Mar. 25, 2014, retrieved from http://www.who.int/mediacentre/news/releases/2014/air-pollution/en/ on Jul. 5, 2016, 4 pages.

Lim et al., "The humidity effect on air flow rates in a critical flow venturi nozzle," Flow Measurement and Instrumentation 22(5):402-405, 2011.

Wilson et al., APTI Course 435 Atmospheric Sampling: Student Manual, United States Environmental Protection Agency, Research Triangle Park, North Carolina, USA, Sep. 1980, Chapter 3, "Air measuring instruments," pp. 3-1 to 3-49. (61 pages).

* cited by examiner

| | \multicolumn{5}{c}{TEMPERATURE (C)} | | | | |
|---|---|---|---|---|---|---|---|---|
| | 100 | 200 | 250 | 300 | 350 | 400 | 500 |
| TIN OXIDE | HYDROGEN, ETHANOL | BUTANE, PROPANE, HYDROGEN-SULPHIDE | | CARBON MONOXIDE | SULPHUR DIOXIDE NITROUS OXIDE | METHANE | |
| TITANIUM OXIDE | | | | | | OXYGEN | |
| TUNGSTUN OXIDE | NITROGEN(x)-OXIDE | | HYDROGEN-SULPHIDE | | SULPHUR DIOXIDE | | |
| TIN OXIDE (La/CuO) | | | | OXYGEN | | | |
| ZINC OXIDE | | | | NITROGEN(x)-OXIDE, HYDROGEN | | | |
| CHROMIUM OXIDE | | | | OXYGEN, ETHANOL | | | |
| INDIUM OXIDE | | | | SULPHUR DIOXIDE NITROGEN(x)-OXIDE, ETHANOL | | PROPANE | CHLORINE |
| CERIUM OXIDE | | | | | OXYGEN, HYDROGEN SULPHIDE | | |

  

FIG. 5

INTEGRATED AIR QUALITY SENSOR THAT DETECTS MULTIPLE GAS SPECIES

BACKGROUND

Technical Field

The present disclosure relates to miniature sensors for use in monitoring air quality to detect gas phase molecules such as carbon dioxide and volatile organic compounds.

Description of the Related Art

It is believed that as many as seven million premature deaths occur annually due to air pollution [*World Health Organization Report, Mar.* 25, 2014]. Air pollution includes both outdoor pollution and poor indoor air quality in enclosed spaces such as, for example, homes, factories, office buildings, and high-density apartment buildings. Indoor air pollution is considered by some experts to be a larger health hazard than outdoor air pollution. Many of the illnesses and deaths associated with air pollution are attributable to the use of solid fuels for heating and cooking in third world countries. However, industrial societies using cleaner forms of energy continue to suffer health effects from indoor pollution. In a typical day, each office worker inhales and processes about fifteen cubic meters of air, exhaling about 350 liters of carbon dioxide ($CO_2$). High levels of volatile organic compounds (VOCs) exist in many buildings constructed using engineered materials that contain glues, dyes, binding agents, adhesives, and the like. Furthermore, cleaning products, solvents, paint and other coatings, furniture, carpeting, and other chemical sources also contribute VOC pollutants. VOCs include such compounds as ethanol, toluene, benzene, formaldehyde, tetrachloroethene (TCE), and methylene chloride.

As heat efficiency of buildings improves and structures have become more airtight, there is less air circulation and a reduction in the exchange of air from outside to inside. As stale air accumulates within a closed space, concentrations of carbon dioxide and VOCs may rise to harmful levels. In some cases, cardio-pulmonary function may be compromised, increasing the risk of heart attacks and strokes. With continued exposure to poor air quality, over time, cancer may be triggered by such airborne toxins. Furthermore, a subtler and more common consequence of poor air quality is that the brain becomes deprived of oxygen, and productivity is reduced. A Harvard study funded by the National Institutes of Health (NIH) shows that a typical indoor $CO_2$ level of about 950 ppm impairs cognitive ability, ultimately lowering worker productivity. [J. G. Allen et al., "Associations of Cognitive Function Scores with Carbon Dioxide, Ventilation, and Volatile Organic Compound Exposures in Office Workers: A Controlled Exposure Study of Green and Conventional Office Environments," Environmental Health Perspectives, DOI:10.1289/ehp.1510037, Oct. 26, 2015]. Consequently, green building practices have been introduced in an attempt to limit the use of VOCs and, in some cases, to require a higher outdoor air ventilation rate to prevent accumulation of both VOCs and $CO_2$.

Maintaining awareness of the levels of VOCs and $CO_2$ present in ambient air is challenging. While some people are particularly sensitive to VOCs and will experience allergic reactions such as headaches, dizziness, and irritation of the eyes, nose, and throat in a high-VOC environment, most people cannot detect hazardous levels of pollution. Because VOCs and $CO_2$ are both odorless, they are generally difficult to detect, and most buildings today are not equipped with multi-species gas sensors. Some portable air quality alert devices that contain $CO_2$ and VOC sensors are available, e.g., AirVisual Node™, Alima™, Atmotube™, Cube Sensor™, and the like; however, such devices tend to be bulky, and each unit that is capable of monitoring a personal sphere of exposure costs hundreds of dollars.

BRIEF SUMMARY

A multi-species micro-sensor device detects multiple gas constituents in ambient air to monitor air quality. In particular, three or more gas species detectors are formed on a single integrated circuit chip, e.g., an application-specific integrated circuit (ASIC) that includes a volatile organic compound (VOC) sensor and a $CO_2$ sensor. The ASIC may also include other types of environmental sensors, as well as a processor and a memory. Such a miniature multi-species sensor chip can be seamlessly and invisibly integrated into many different products. For example, a multi-species gas sensor chip can be incorporated into fixtures, such as desktop computers or displays, to monitor an individual's work environment. In addition, an integrated sensor chip can be incorporated into mobile devices such as laptop computers, smart phones, clothing, watches, and other accessories to function as a personal monitoring device for air quality. Such an integrated multi-species gas sensor can continuously monitor an air quality index that includes levels of various gas species along with humidity, temperature, and the like.

An integrated multi-species gas micro-sensor is smaller, more accurate, and less expensive than existing air quality sensors. The multi-species gas micro-sensor includes a VOC sensor in the form of a conformal thin film less than 0.2 micron thick. The multi-species gas micro-sensor also includes a heater having a low temperature coefficient of resistance.

BRIEF DESCRIPTION OF THE SEVERAL VIEWS OF THE DRAWINGS

In the drawings, identical reference numbers identify similar elements or acts unless the context indicates otherwise. The sizes and relative positions of elements in the drawings are not necessarily drawn to scale.

FIG. 5 is a data table listing temperatures at which various gas species can be detected using different sensor materials, according to an embodiment as described herein.

DETAILED DESCRIPTION

Figure 1:
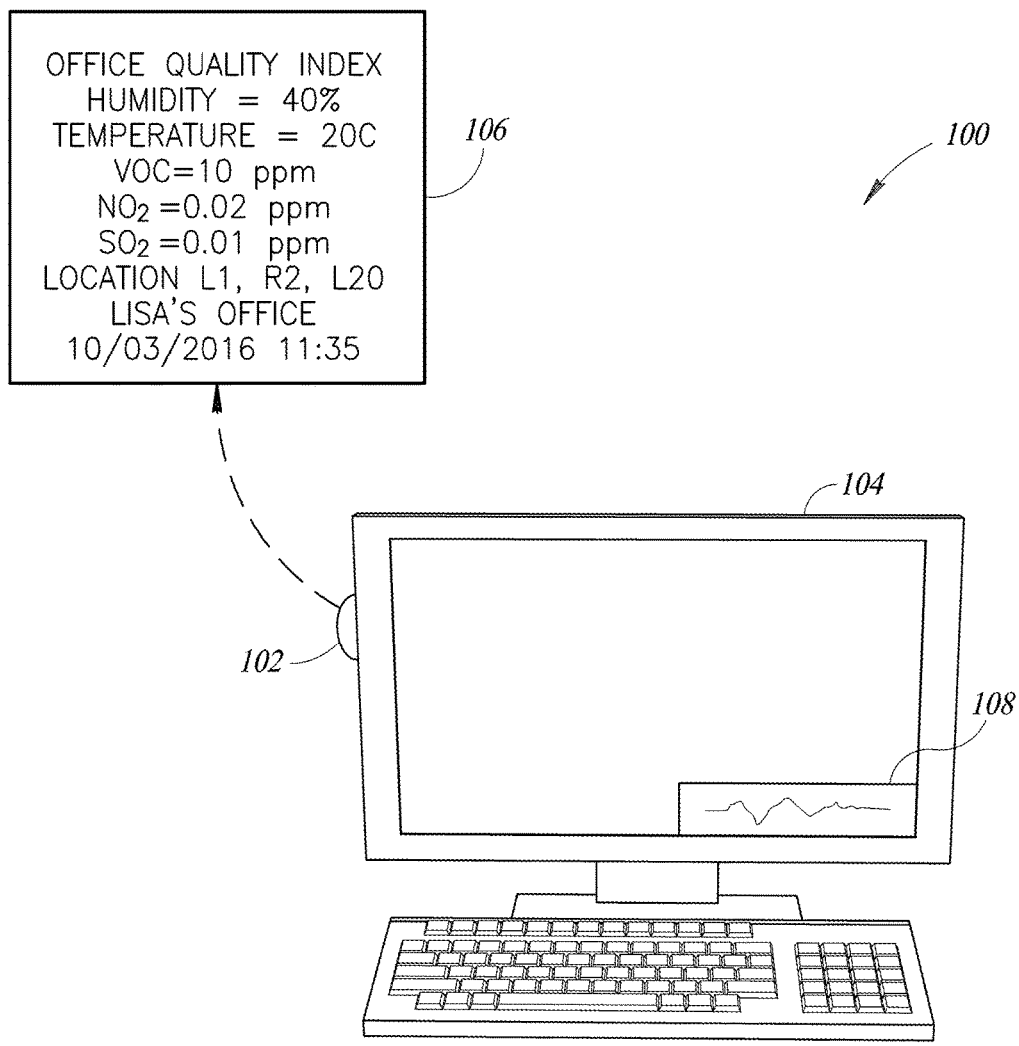
FIG. 1 is a pictorial view of a microelectronic air quality monitor in use, according to an embodiment as described herein.

In the following description, certain specific details are set forth in order to provide a thorough understanding of various aspects of the disclosed subject matter. However, the disclosed subject matter may be practiced without these specific details. In some instances, well-known structures and methods comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "In an embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like and one layer may be composed of multiple sub-layers.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to air quality sensors that have been produced; however, the present disclosure and the reference to certain materials, dimensions, and the details and ordering of processing steps are exemplary and should not be limited to those shown.

Turning now to the Figures, FIG. 1 shows a workstation 100 equipped with an air quality monitor 102, according to an embodiment of the present disclosure. The workstation 100 represents a fixture such as a desktop computer, a laptop computer, a kiosk, a wall-mounted display, or the like. The workstation 100 includes a display 104 that presents air quality data in the form of a statistical summary 106 and a trend chart 108. The air quality data is sensed locally by the air quality monitor 102 and is then analyzed by electronic components for presentation on the display 104. The electronic components that process and analyze the air quality data may be located within the workstation 100, or at a remote location communicatively coupled to the workstation 100 by a wired or wireless connection, e.g., a network connection. The air quality monitor 102 may be a fixed component of the workstation 100, or the air quality monitor 102 may be a mobile unit that is removably attached to the workstation 100. In one embodiment, the air quality monitor 102 may be part of a smart phone, a tablet computer, a laptop computer, a watch, a pendant, an article of clothing, or another type of mobile unit associated with a user of the workstation 100, wherein the air quality monitor 102 is communicatively coupled to the workstation 100 only while a particular user is working at the workstation 100. The air quality monitor 102 may maintain a user history of locations and associated air quality data to monitor the user's exposure to certain air pollutants. Alternatively, the air quality monitor 102 may maintain a history of air quality data specific to a fixed location of the workstation 100.

In one embodiment, the statistical summary 106 presented on the display 104 includes a humidity reading, a temperature reading, a volatile organic compound concentration reading, a location, a time stamp, and an overall office air quality index. The statistical summary 106 is exemplary and may include more or fewer data items than are shown in FIG. 1. One or more of the data items may be displayed as a time series graph on the trend chart 108 that occupies a portion of the display 104 so that a user of the workstation 100 can be informed of local air quality in real time. The trend chart 108 may display time trends of individual data items in succession, on a rotating basis. Alternatively, a plurality of time trends may be displayed simultaneously on the trend chart 108. The trend chart 108 may be configurable by the user or by a system administrator.

Figure 2:
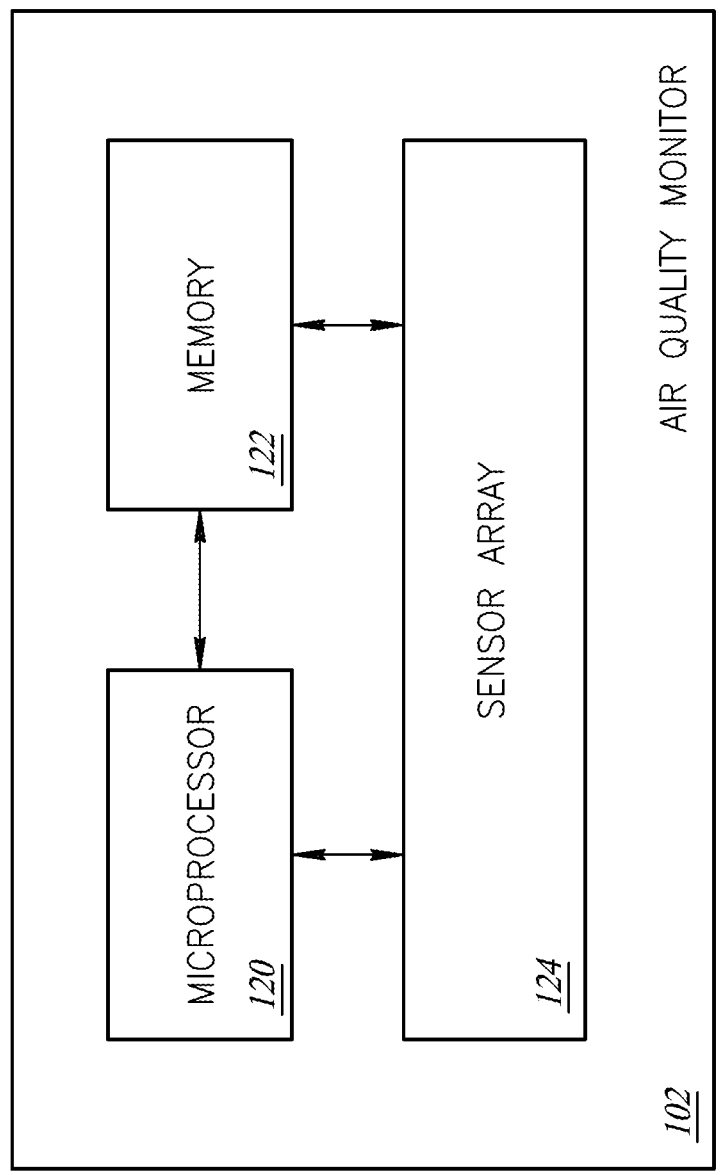
FIG. 2 is a block diagram of the microelectronic air quality monitor shown in FIG. 1, according to an embodiment as described herein.

FIG. 2 shows components of the air quality monitor 102, according to an embodiment of the present disclosure. The air quality monitor 102 is a microelectronic device that includes at least a microprocessor 120, an electronic memory 122, and a micro-sensor array 124. The microprocessor 120 is communicatively coupled to the electronic memory 122 and the micro-sensor array 124. The electronic memory 122 is configured to store instructions for execution by the microprocessor 120 and to store data received from the micro-sensor array 124. The micro-sensor array 124 may also be coupled directly to the electronic memory 122. Any one of the communication paths among components of the air quality monitor 102 may support wired or wireless data communication. The micro-sensor array 124 may be an application-specific integrated circuit (ASIC) chip. A portion or all of the electronic memory 122 may be implemented on board the ASIC chip. Furthermore, all components of the air quality monitor may be co-integrated as a system-on-chip (SOC).

The micro-sensor array 124 may be implemented as described in a related patent document entitled, "Integrated SMO Gas Sensor Module," [U.S. patent application Ser. No. 14/334,572 to Shankar et al., published as U.S. Patent Publication No. 2016/0018356, hereinafter "Shankar"], which is assigned to the same entity as the present patent application, and is herein incorporated by reference in its entirety. Alternatively, the micro-sensor array 124 may be implemented as described herein, which implementation has some features that differ from those of Shankar. Alternatively, the micro-sensor array 124 may be implemented so as to combine certain features of Shankar's gas sensor with certain other features of the gas sensor as described herein. In one embodiment, the entire air quality monitor 102 is on a single substrate 222 (see FIG. 7). In other embodiments, the micro-sensor array 124 is on its own silicon substrate and the microprocessor 120 and the electronic memory 122 are together on a single silicon substrate.

Figure 3A:
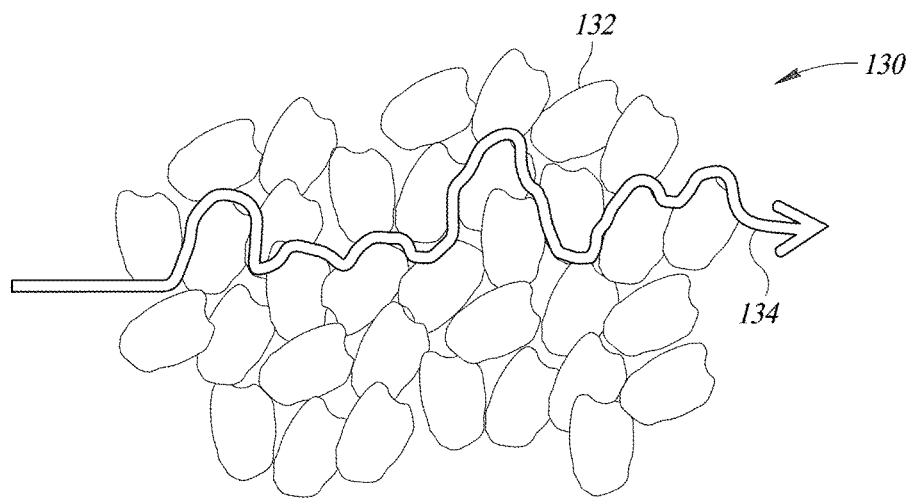
FIG. 3A is a pictorial view of a thick sensor material in powder form that is structured to sustain a bulk chemical reaction, according to the prior art.
Figure 3B:
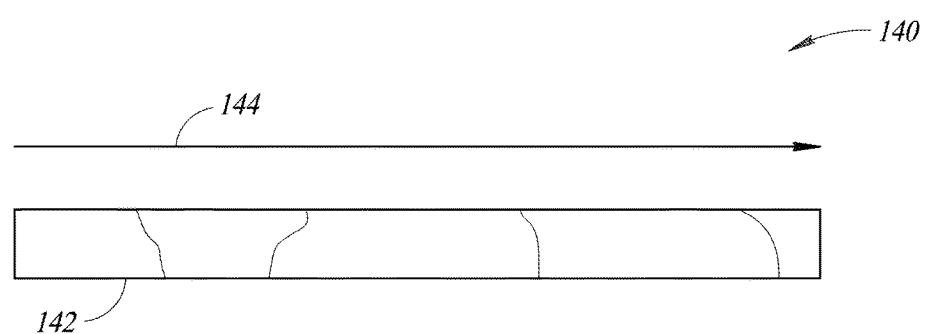
FIG. 3B is a pictorial view of a sensor material in the form of a thin film that is structured to sustain a surface chemical reaction, according to an embodiment as described herein.

FIGS. 3A, 3B contrast the prior art with the present invention for providing an air quality sensor. FIG. 3A shows a bulk sensor material 130, known in the art. The bulk sensor material 130 is in the form of a powder that is structured to sustain a chemical reaction with ambient air. The bulk sensor material 130 is made up of particles 132 that may include multi-crystalline grains of a reactive material. Ambient gas can flow through bulk sensor material, for example, along a circuitous path 134, which facilitates contact between the ambient gas molecules and surfaces of the particles 132. The bulk sensor material 130 may be, for example, tin oxide ($SnO_2$) having a thickness in the range of about 5 μm to 20 μm. The bulk sensor material 130 is typically sintered at a temperature of 600 C. The bulk sensor material 130 is a known system and will therefore not be further described. It is large and bulky, and does not fit on a silicon substrate.

FIG. 3B shows a thin film gas sensing material 140, suitable for use in the micro-sensor array 124, according to an embodiment of the present disclosure that is an improvement over the sensor of FIG. 3A. The thin film gas sensing material 140 has a structure that supports surface conduction of ambient gas along a substantially straight path 144, and a surface reaction between the ambient gas and a dense, multi-crystalline thin film 142 that is made of a thin film gas sensing material 140. In one example, the thin film 142 is a tin oxide ($SnO_2$) film of thickness 100 nm, about 100 times thinner than the bulk sensor material 130. Other gas sensing materials that can be used as the thin film 142 include zinc oxide ($ZnO_2$) and indium oxide ($In_2O_3$). The thin film 142 may be formed by sputter deposition, followed by sintering at a low temperature of 400 C. The resulting thin film 142 is so dense that it is classified as a ceramic as opposed to a powder. Part or all of the thin film 142 may then be capped with a thin coating of platinum (Pt). The sensitivity of thin film gas sensing materials 140 to various gases that may be present in ambient air is known to change as a function of temperature. The platinum coating may assist in transferring heat to the thin film 142.

Figure 4:
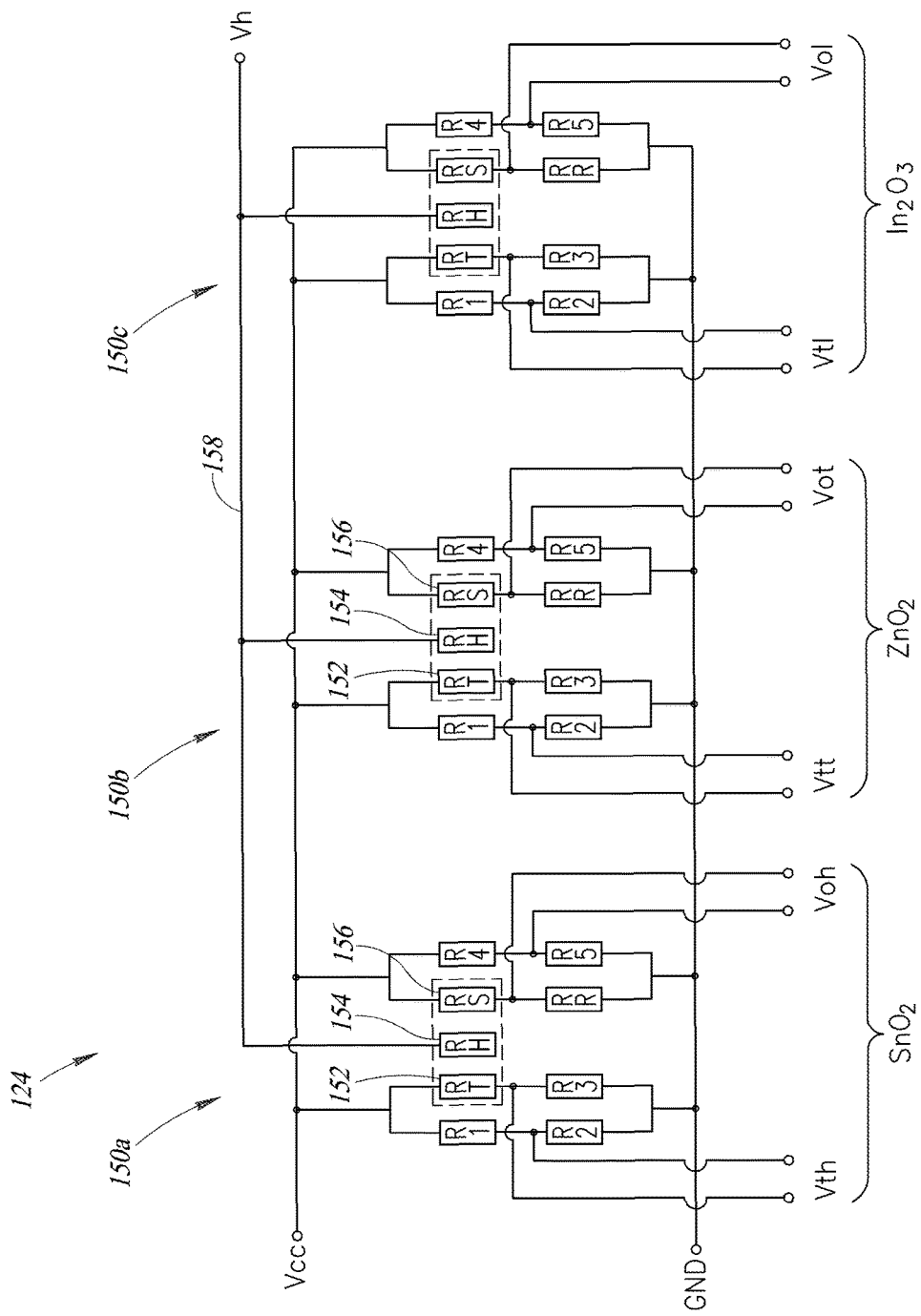
FIG. 4 is a circuit schematic of a multi-species gas sensor array including sensors for detecting three different gas species according to an embodiment as described herein.

FIG. 4 shows a circuit schematic of the micro-sensor array 124, according to an embodiment of the present disclosure. Elements of the micro-sensor array 124, (three shown: 150a, b, c) include a temperature sensor 152, a resistive heater 154, and a gas sensor 156 that are formed together on a common substrate. The resistive heater 154 is electronically controlled by the microprocessor according to programmed instructions, so as to tune the gas sensor 156 to be sensitive to a particular gas. The temperature sensor 152 can be used as a feedback control device for automatically adjusting the resistive heater 154. Power is delivered to the resistive heaters 154 via a heater signal line 158 that is driven at a voltage $V_h$. The gas sensor 156 includes the thin film 142 in the form of the thin film gas sensing material 140 shown in FIG. 3B. The temperature of each gas sensor 156 is determined by the voltage $V_h$ and a resistance $R_H$ of an associated resistive heater 154. Each element of the micro-sensor array 124 can be operated within a different temperature range when the resistances $R_H$ have different values. This can be accomplished by using different sensing materials in the different elements of the micro-sensor array 124. For example, a first element 150a of the micro-sensor array 124 may include tin oxide ($SnO_2$) as an active sensing material and may be operated within a temperature range of 400 C-500 C, while a second element 150b of the micro-sensor array 124 may include $ZnO_2$ as an active sensing material and may be operated in a temperature range of 300 C-350 C. In one embodiment, each temperature sensor 152 is configured as a Wheatstone bridge that includes three fixed resistors R1, R2, and R3. To control dissipation of heat and power consumption, heating is done in a confined manner as explained below.

FIG. 5 shows a table 300 that lists which gases can be detected by VOC sensors based on material and operating temperature, according to an embodiment of the present disclosure. For example, when a VOC sensor made of $SnO_2$ is heated to an operating temperature of 100 C, it is capable of detecting hydrogen gas. But when the $SnO_2$ sensor is heated to an operating temperature of 300 C, it will detect carbon monoxide (CO), and at 400 C, it will detect methane. When a VOC sensor made of $ZnO_2$ is heated to 300 C, it detects nitrogen oxide ($NO_2$). When a VOC sensor made of $InO_2$ is heated to 300 C, it will detect sulphur dioxide ($SO_2$). Other sensor materials such as the various oxide compounds listed in the first column of the table 300 can be substituted for, or used in addition to, $SnO_2$, $ZnO_2$, and $InO_2$ in the VOC sensors. Accordingly, each one of the VOC sensors in the micro-sensor array 124 can be tuned to sense a selected gas by controlling the associated heater that is disposed adjacent to the sensor. It is advantageous to construct the VOC sensor array to ensure that the heat is confined to the local region of the VOC sensor and that it remains at the desired temperature over time, and to sustain the accuracy of the sensor elements.

In one embodiment, the same physical material is heated to different temperatures at different times to sense different gases. In one example, at a first time, the $SnO_2$ layer is heated to about 200 C to detect butane and propane. At a later time, the very same material is heated to about 300 C to detect CO. The local temperature sensor adjacent to the material provides a feedback signal to ensure that the $SnO_2$ material is at the desired temperature for sensing the selected gas.

Figure 6:
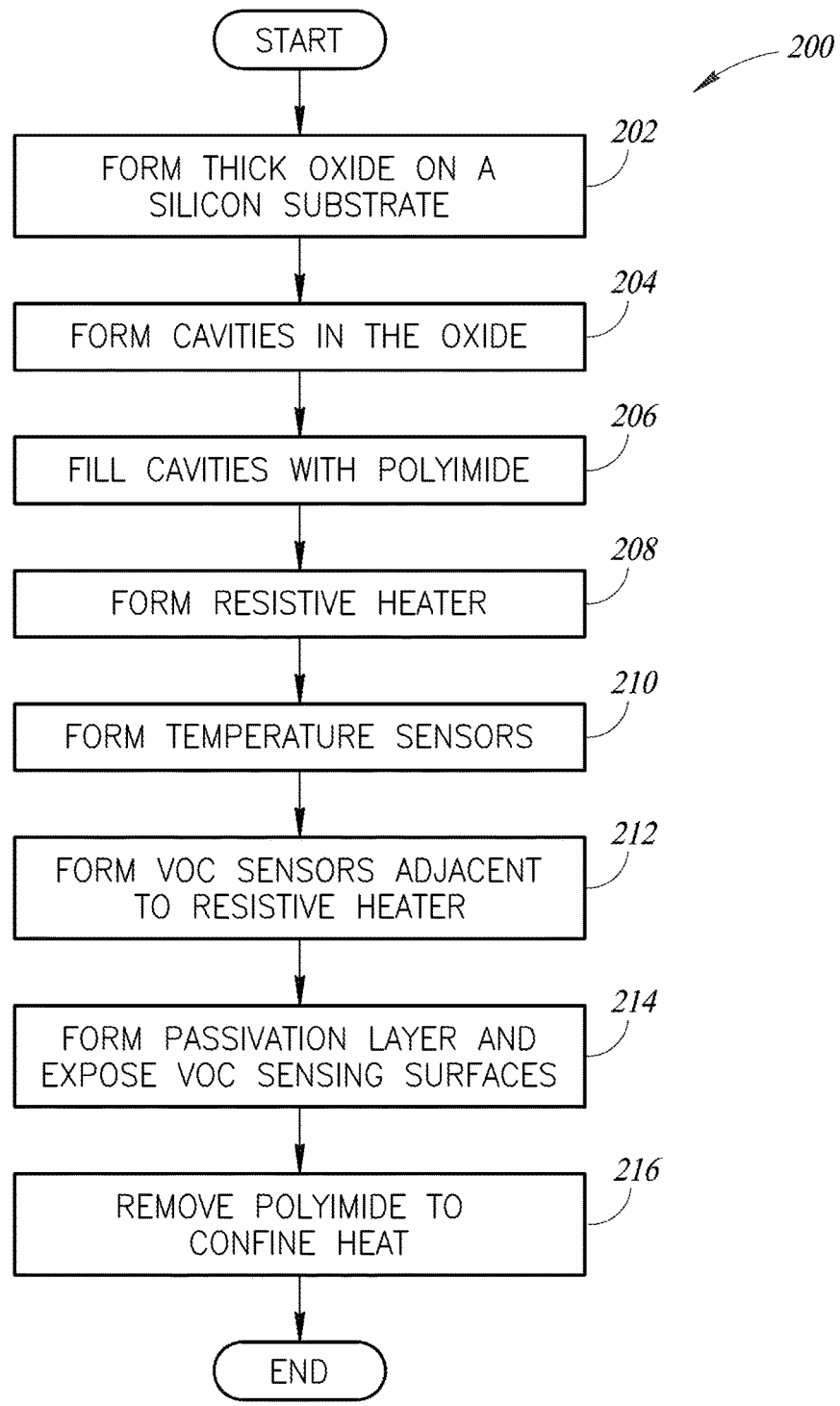
FIG. 6 is a flow diagram showing steps in a method of fabricating a multi-species gas micro-sensor according to an embodiment as described herein.

FIG. 6 is a flow diagram showing a sequence of steps in a method 200 for fabricating the sensor array shown in FIG. 4, according to an embodiment of the present disclosure. All of the steps in the method 200 can be carried out at temperatures at or below 400 C. With reference to FIGS. 7-10, the multi-species gas sensors 156, suitable for detecting VOCs, are formed adjacent to resistive heaters 154.

At 202, a thick oxide 224 is formed on a substrate 222 using, for example, a conventional thermal growth process. The substrate 222 may be, for example, a silicon substrate or a glass substrate having a thickness in the range of about 500 µm to 600 µm. The thick oxide 224 has a thickness in the range of about 3 µm to 10 µm.

At 204, cavities about 2 µm deep are formed in the thick oxide 224 by patterning the thick oxide 224, using conventional photolithography and etching techniques. For example, the thick oxide 224 may be patterned using a photoresist and etched using a wet chemical etchant such as hydrofluoric acid (HF). The cavities may have sloped sides.

Figure 7:
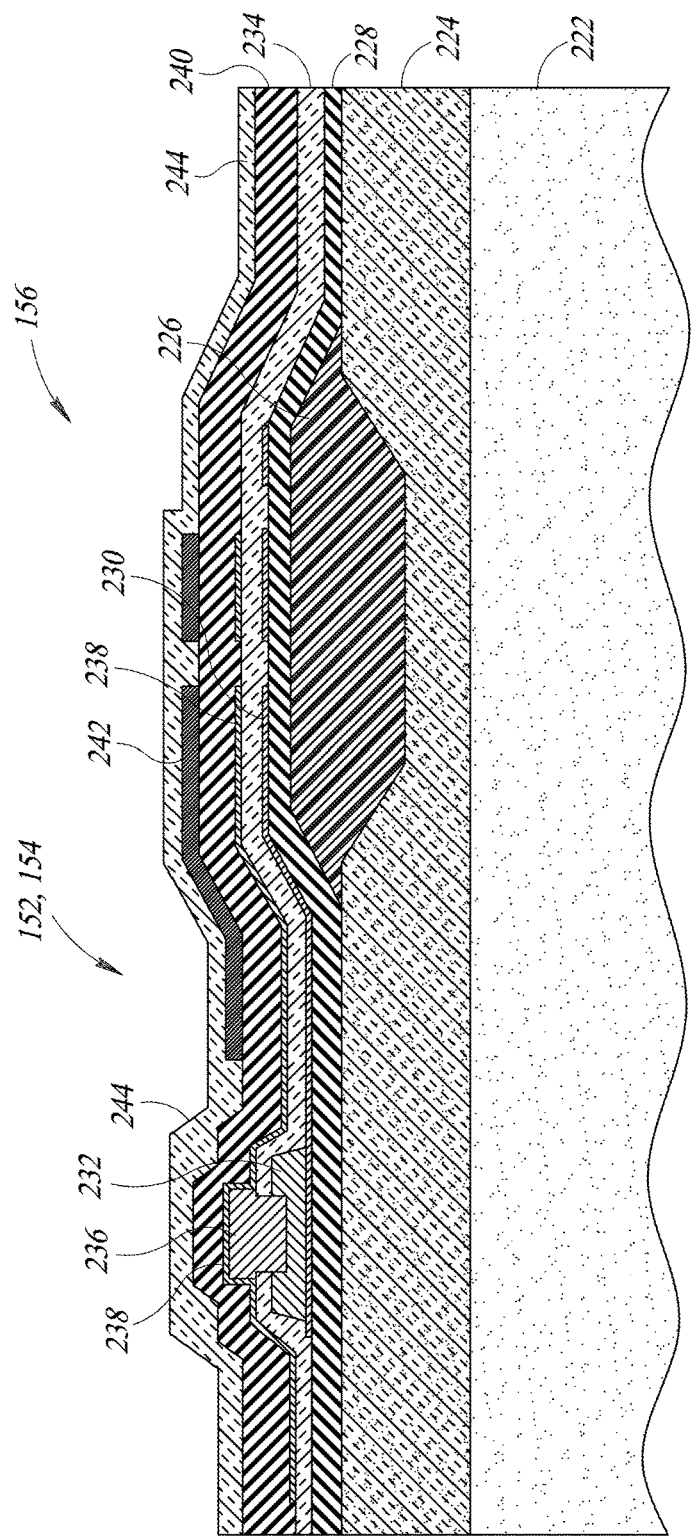
FIGS. 7-10 are cross-sectional views of a multi-species gas sensor following steps of the fabrication method shown in FIG. 6.

At 206, the cavities are filled with a 4-µm thick layer 228 of polyimide to form polyimide wells 226 as shown in FIG. 7. The polyimide material can be, for example, a material such as HD8220 available from Fujifilm corporation of Tokyo, Japan. The polyimide wells 226 can be cured at a temperature of 325 C for one hour to reduce the thickness to 3 µm, wherein about 2 µm of the polyimide layer is below the surface of the thick oxide 224 and about 1 µm of the polyimide layer is above the surface of the thick oxide 224. Next, a 300-nm thick silicon nitride capping layer 228 (e.g., $Si_3N_4$) is formed on top of the polyimide wells 226 using a conventional method of conformal thin film deposition.

At 208, the resistive heaters 154 are formed as 150-nm thick heating elements 230 made of tantalum aluminum (TaAl), according to one embodiment of the present disclosure. TaAl features a low thermal coefficient (TCR) that results in a stable resistance. A first metal layer is formed on top of the heating elements 230 and patterned to form contacts 232 to the heating elements 230. The contacts 232 can be made of any metal suitable for use as integrated circuit interconnects such as, for example, aluminum copper (AlCu) having a thickness of about 500 nm. The contacts 232 may be etched so as to have sloped sides. The contacts 232 and the heating elements 230 are covered with a first conformal interlayer dielectric (ILD) 234, e.g., another 300-nm thick layer of $Si_3N_4$. Vias are then formed in the conformal ILD 234 and filled with a second metal layer 236 made of AlCu having a thickness of 500 nm.

At 210, temperature sensing elements 238 are formed by patterning a high-TCR thin film that is conformally deposited over the second metal layer 236. The temperature sensing elements 238 can be made of, for example, platinum (Pt) having a thickness of about 20 nm. A second conformal ILD 240 is then deposited over the temperature sensing elements 238. The second conformal ILD 240 can be 30 nm of $Si_3N_4$. In some embodiments, the temperature sensing elements 238 are optional and may be omitted, depending on a desired level of calibration and accuracy.

At 212, multi-species gas sensors are formed adjacent to the resistive heaters 154. A first VOC sensor 242 is formed as a patterned tin oxide ($SnO_2$) film having a thickness in the range of about 30 nm to 100 nm. The first VOC sensor 242 is formed over selected ones of the polyimide wells 226. A first VOC sensor cap 244 is formed as a 50-nm thick $SiO_2$ film that is conformally deposited over the first VOC sensor 242.

Figure 8A:
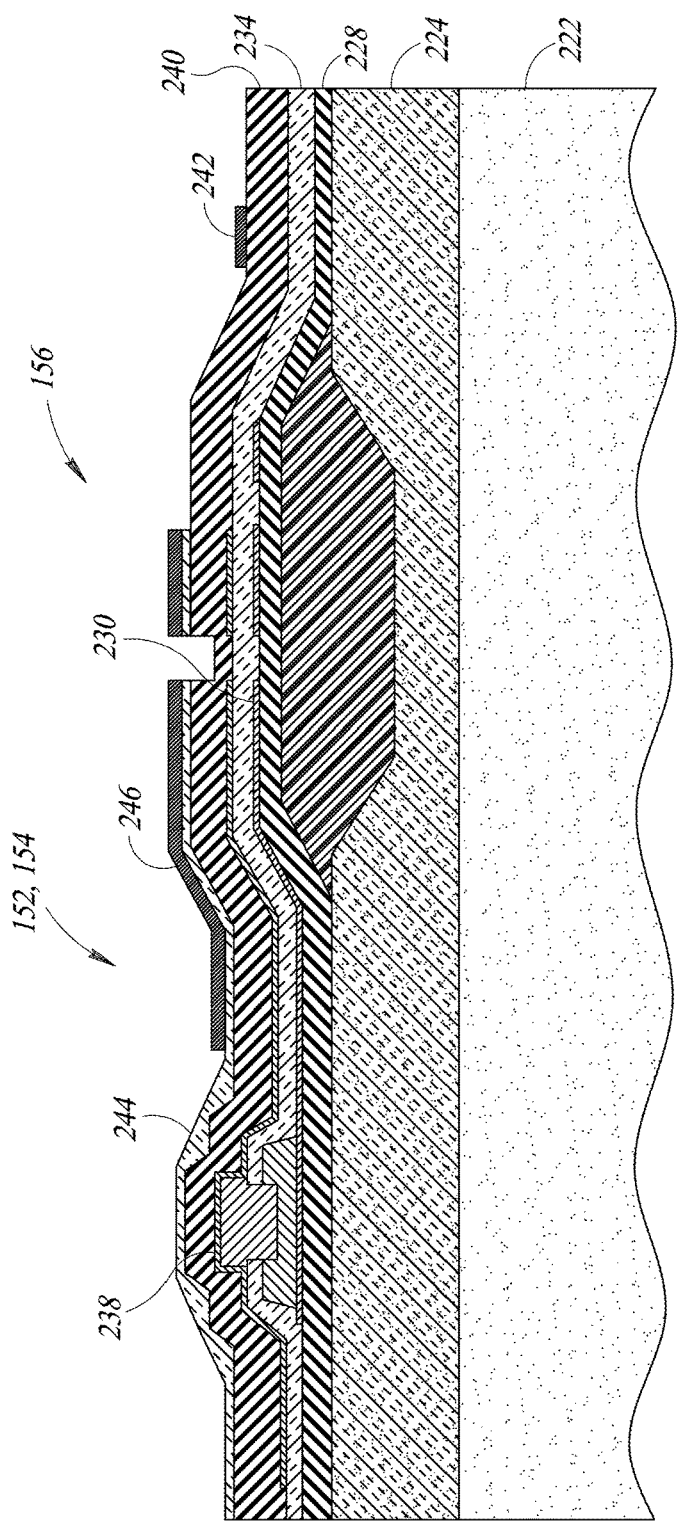

A second VOC sensor 246 is formed at a different location on the same substrate 222, as shown in FIG. 8A. In one embodiment, the second VOC sensor 246 is a patterned zinc oxide ($ZnO_2$) film having a thickness of about 100 nm. When the $ZnO_2$ film is being deposited and patterned, the area of the first sensor 242 is covered with the appropriate mask to protect it while sensor layer 246 is being formed. By selectively patterning the $ZnO_2$ film, the second VOC sensor 242 can be formed over different ones of the polyimide wells 226 than the $SnO_2$ film that is used for the first VOC sensor 242. In this way, a single process flow can be used to fabricate different types of VOC sensors, each sensor being paired with a heater and a temperature sensor. A second VOC sensor cap 248 is formed as a 50-nm thick $SiO_2$ film that is conformally deposited over the second VOC sensor 246, as shown in FIG. 8B.

Figure 8B:
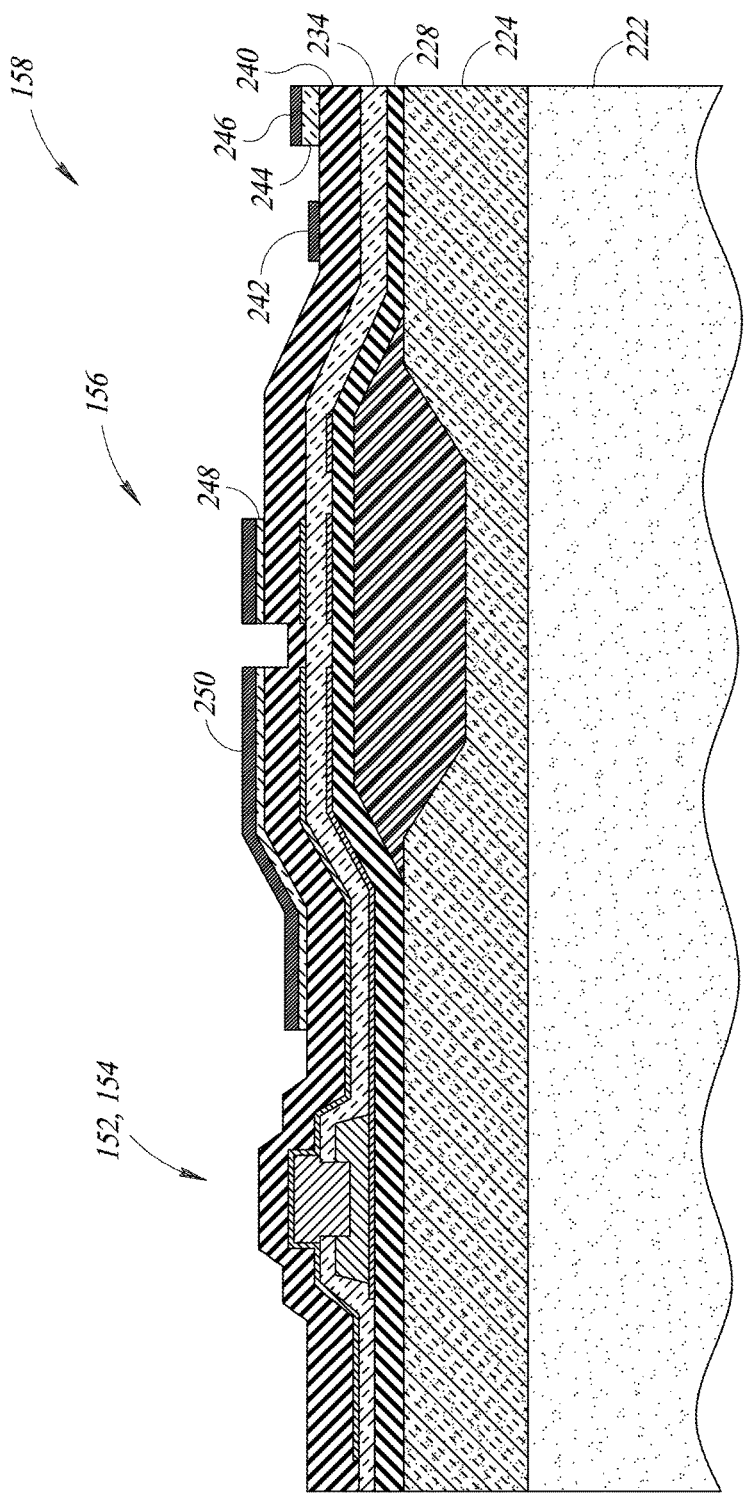

A third VOC sensor 250 is formed as a patterned indium oxide ($In_3O_3$) film having a thickness of about 150 nm, as shown in FIG. 8B. The third VOC sensor 250 is formed over selected ones of the polyimide wells 226 at different locations on the same substrate 222. The first and second VOC sensor films are masked in the patterning process for the third sensor 250.

The layers 242, 246 and 250 are specific examples of the thin film 142 shown and described in FIG. 3B. Other materials besides the specific ones shown in FIGS. 7-8B may be used to sense different gases as explained with respect to FIG. 5.

Figure 9:
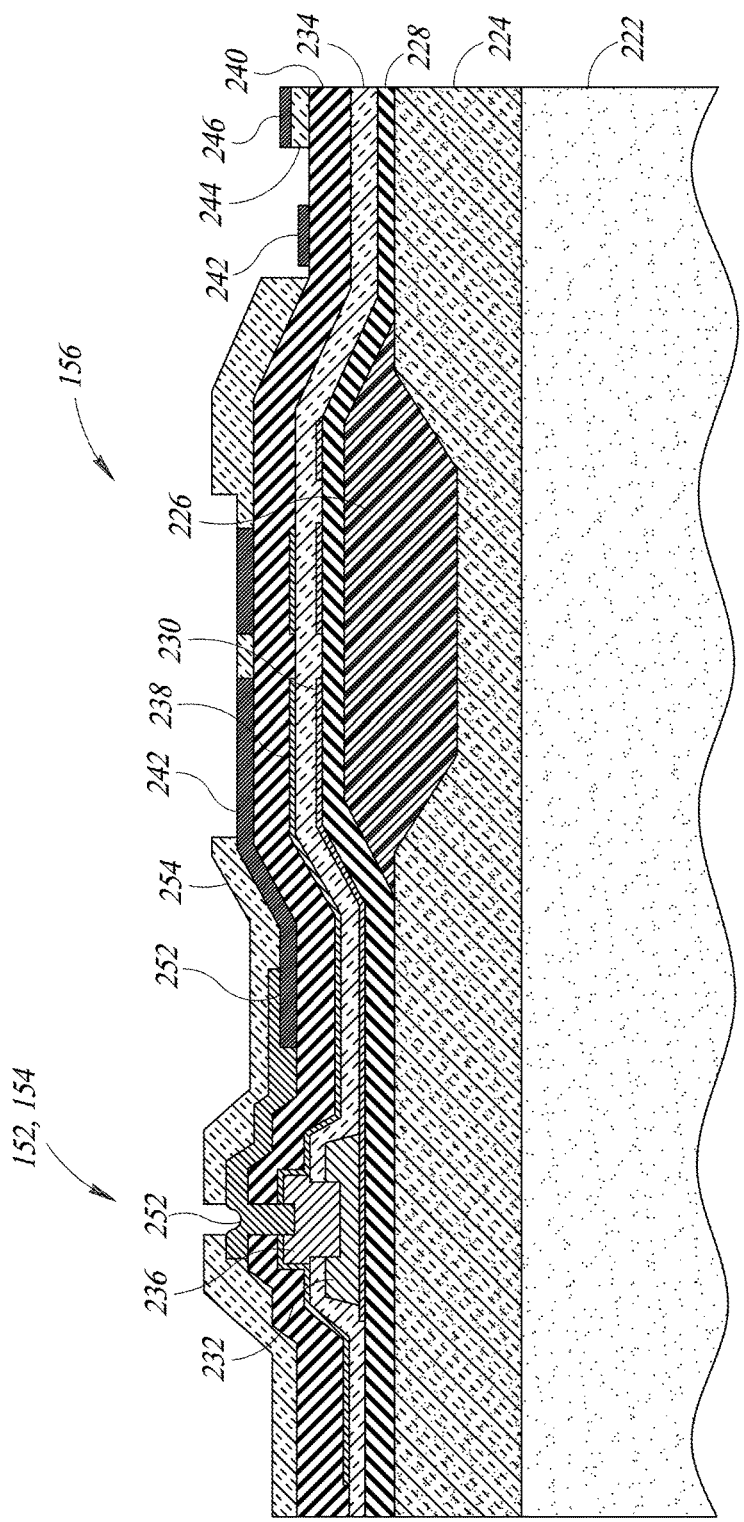

With reference to FIG. 9, vias are formed in the second conformal ILD 240 and are filled with a third metal layer 252 made of AlCu having a thickness of about 500 nm.

Figure 10:
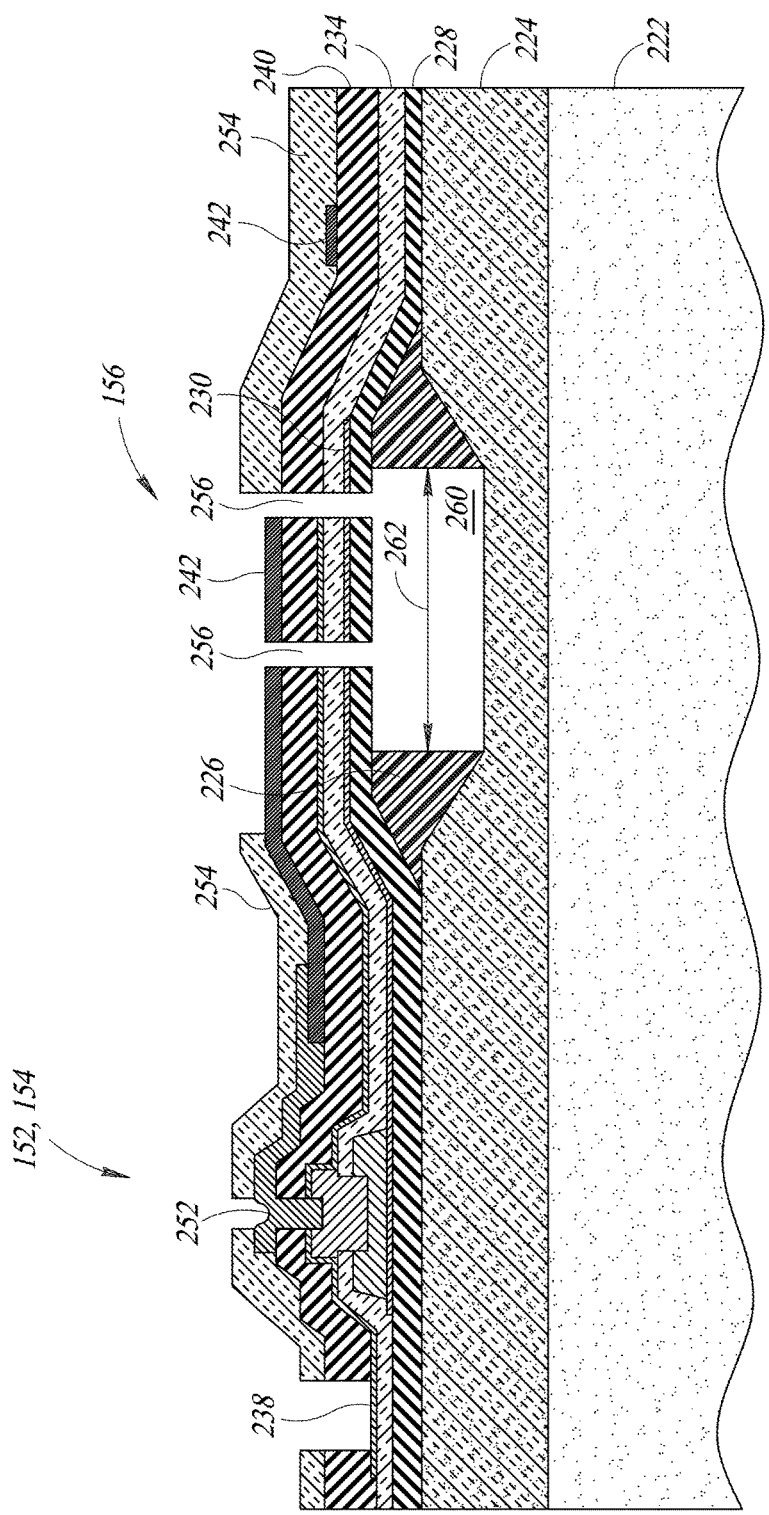

At 214, a passivation layer 254 is formed over the third metal layer 252 and the VOC sensors, as shown in FIG. 10. The passivation layer 254 may be made of SiN. The passivation layer 254 is patterned to expose the VOC sensors, and to provide a signal path via the various metal layers to access the temperature sensing elements 238 and the contact 232 to the heating element 230. Each one of the first, second, and third VOC sensors has an exposed active sensing area of about 200 $\mu m^2 \times 100$ $\mu m^2$.

At 216, some of the polyimide material is removed from the polyimide wells 226. Openings 256 are formed by etching through the VOC sensor layers and ILD layers to expose the polyimide wells 226. A second film removal step is then performed to remove polyimide material from the polyimide wells 226, leaving air pockets 260 underneath the heating elements 230. The air pockets 260 have widths 262. The widths 262 of the air pockets are desirably much larger than the openings 256, so that air is effectively trapped within the air pockets 260 while being maintained at an atmospheric pressure of the ambient air. A curing step can then be performed at 400 C for two hours at atmospheric pressure to shrink and harden polyimide material remaining in the polyimide wells 226, thereby solidifying the walls of the air pockets 260. The air pockets 260 provide thermal insulation to trap heat produced by the heating elements 230 so that the heat is spatially confined within a local vicinity of the adjacent VOC sensor and is not transmitted to other VOC sensors in the micro-sensor array 124.

Figure 11:
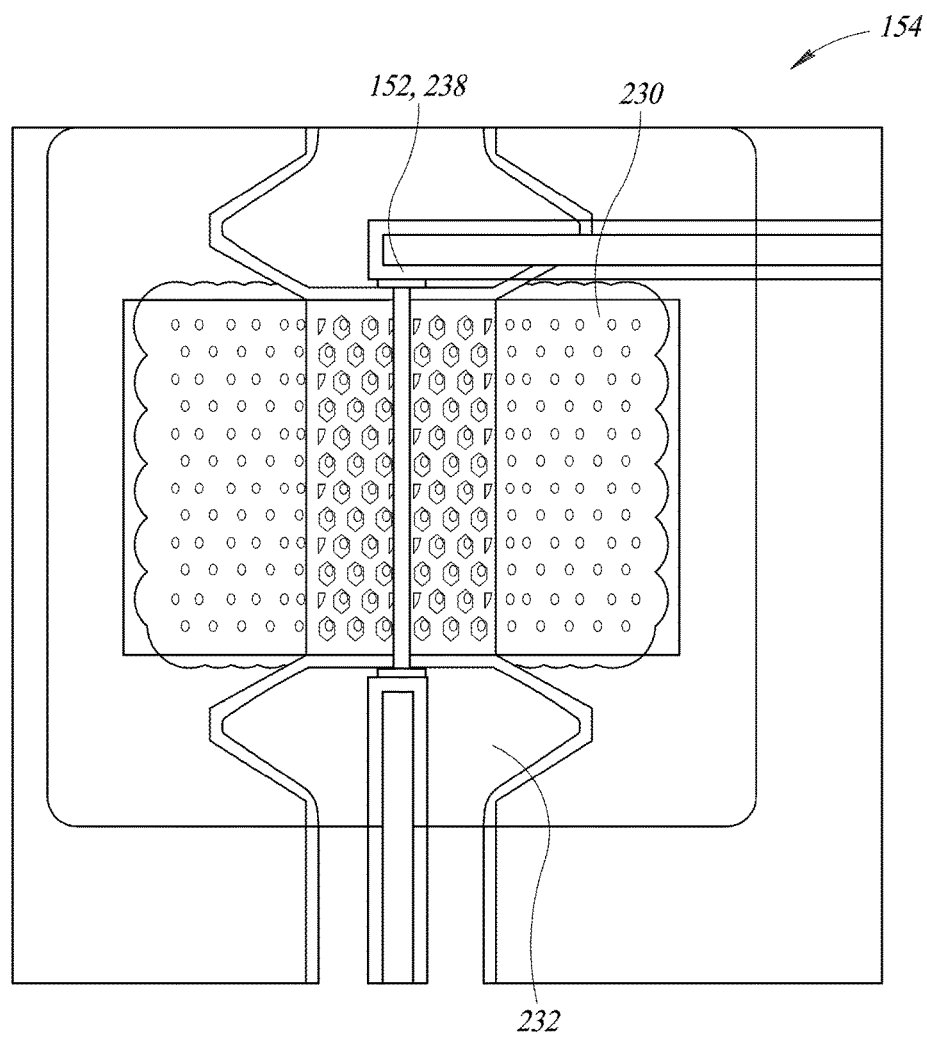
FIG. 11 is a top plan view of a VOC sensor, according to one embodiment as described herein.

FIG. 11 shows a top plan view of an exemplary temperature sensor 152 and an exemplary resistive heater 154, according to an embodiment of the present disclosure. The resistive heater 154 can be designed as a metal mesh heating element 230 in which the openings 256 lead to the air pockets 260 located below the heating element 230. The contact 232 provides electrical power to the heating element 230. The temperature sensor 152 is disposed in a layer above the heating element 230, and extends to a position directly below the VOC sensor.

Figure 12:
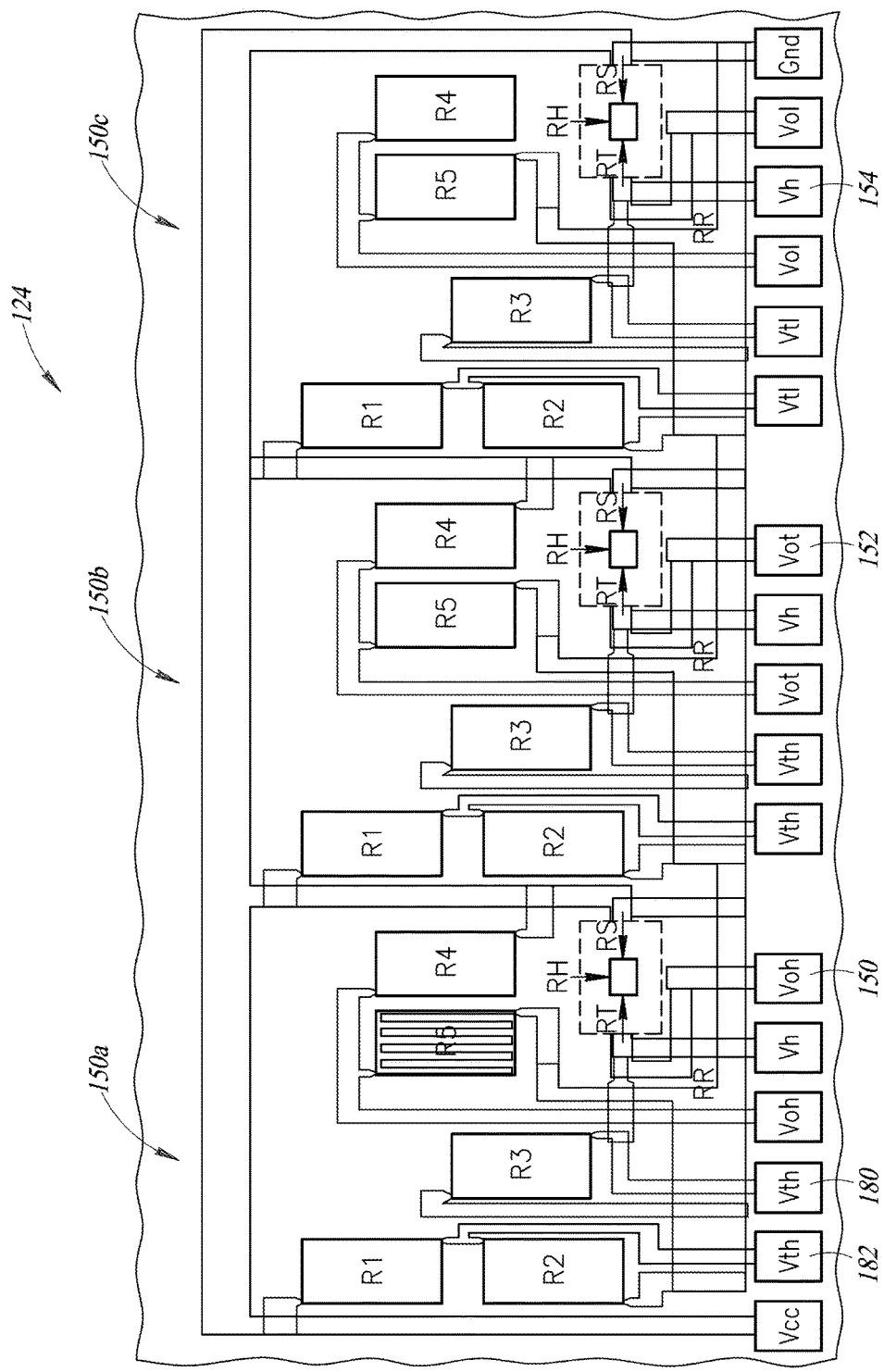
FIG. 12 is a top plan view of a chip layout corresponding to the sensor array shown in FIG. 4.

FIG. 12 shows a physical layout in silicon of the entire circuit of the micro-sensor array 124 on the substrate 222, according to an embodiment of the present disclosure. The view in FIG. 12 shows three elements, on a single integrated circuit, of the micro-sensor array 124 that correspond to the three elements shown schematically in FIG. 4. Contact pads 180 provide electrical connections to the micro-sensor array elements 150a, b, c, for access by the microprocessor 120 and the electronic memory 122. Electrical signal paths 182 are also indicated in FIG. 12. Resistors R1, R2, R3, and so on, are shown as serpentines. A total footprint of the exemplary three-element array shown in FIG. 12 is 2.6 mm×0.9 mm=2.34 mm$^2$.

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

It will be appreciated that, although specific embodiments of the present disclosure are described herein for purposes of illustration, various modifications may be made without departing from the spirit and scope of the present disclosure. The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
  a substrate; and
  a plurality of gas species sensors arranged as elements of a single integrated circuit array, each of the plurality of gas species sensors including:
    a cavity in the substrate;
    a gas sensitive material configured to detect a particular gas species;
    a heating element adjacent to the gas sensitive material; and
    a temperature sensing element between the gas sensitive material and the heating element, the cavity, the gas sensitive material, the heating element, and temperature sensing element being aligned with each other.

2. The device of claim 1 wherein the gas sensitive material is formed in a reactive layer of a metal oxide semiconductor structure, and the reactive layer is less than 500 nm thick.

3. The device of claim 1 wherein the gas sensitive material is a ceramic.

4. The device of claim 3 wherein the ceramic includes one or more of $SnO_2$, $ZnO_2$, or $In_2O_3$.

5. The device of claim 3 wherein the gas sensitive material is less than 200 nm thick.

6. The device of claim 1 wherein each of the plurality of gas species sensors includes a through hole that extends through the gas sensitive material, the heating element, and the temperature sensing element.

7. The device of claim 1, further comprising:
  a passivation layer on the plurality of gas species sensors, the passivation layer including openings that overlie the gas sensitive material of the plurality of gas species sensors.

8. A microelectronic air quality monitor, comprising:
  a semiconductor substrate;
  a micro-sensor array formed on the semiconductor substrate, the micro-sensor array having a plurality of sensor elements, each of the plurality of sensor elements including a respective heater, a respective gas micro-sensor configured to detect a presence of a particular gas species in ambient air, and a respective temperature sensor between the respective heater and the respective gas micro-sensor;
  a microprocessor communicatively coupled to the micro-sensor array; and
  an electronic memory communicatively coupled to the microprocessor, the electronic memory configured to store instructions for execution by the microprocessor.

9. The microelectronic air quality monitor of claim 8 wherein the semiconductor substrate is a glass substrate.

10. The microelectronic air quality monitor of claim 8 wherein the gas micro-sensors are temperature sensitive and can be selectively tuned to operate at different temperatures.

11. The microelectronic air quality monitor of claim 8, wherein the temperature sensor is communicatively coupled to the microprocessor.

12. A method, comprising:
  forming a first heater in a first region of an integrated circuit chip;
  forming a first temperature sensor in the first region and on the first heater;
  forming a first gas sensitive material in the first region and on the first temperature sensor;
  forming a through hole through the first heater and the first gas sensitive material;
  forming a second heater in a second region of the integrated circuit chip;
  forming a second temperature sensor in the second region and on the second heater; and
  forming a second gas sensitive material in the second region and on the second temperature sensor.

13. The method of claim 12 wherein each of the first and second heaters includes a low-TCR heating element including tantalum aluminum.

14. The method of claim 12 wherein each of the first and second gas sensitive materials includes one or more of zinc oxide (ZnO), indium oxide ($In_3O_3$), and tin oxide ($SnO_2$).

15. The method of claim 12, further comprising:
  forming a first air pocket, the first gas sensitive material being spaced from the first air pocket by the first heater; and
  forming a second air pocket, the second gas sensitive material being spaced from the second air pocket by the second heater.

16. The method of claim 12 wherein the first and second gas sensitive materials are made of different materials.

17. A device, comprising:
  a substrate; and
  a plurality of gas species sensors arranged as elements of a single integrated circuit array, each of the plurality of gas species sensors including:

a cavity in the substrate;
a gas sensitive material configured to detect a particular gas species;
a heating element adjacent to the gas sensitive material; and
a temperature sensing element adjacent to the gas sensitive material, the cavity, the gas sensitive material, the heating element, and the temperature sensing element being aligned with each other, each of the plurality of gas species sensors including a through hole that extends through the gas sensitive material, the heating element, and the temperature sensing element.

18. The device of claim 17 wherein the temperature sensing element is between the gas sensitive material and the heating element.

19. The device of claim 17, further comprising:
a passivation layer on the plurality of gas species sensors, the passivation layer including openings that overlie the gas sensitive material of the plurality of gas species sensors.

\* \* \* \* \*